United States Patent [19]

Alexeev

[11] 4,316,292
[45] Feb. 23, 1982

[54] ARTIFICIAL CRYSTALLINE LENS

[76] Inventor: Boris N. Alexeev, Bolshoi Tatarsky pereulok, 4, kv. 88, Moscow, U.S.S.R.

[21] Appl. No.: 92,832

[22] Filed: Nov. 9, 1979

[51] Int. Cl.³ .............................. A61F 1/16; A61F 1/24
[52] U.S. Cl. ............................................................ 3/13
[58] Field of Search ................................................. 3/13

[56] References Cited

U.S. PATENT DOCUMENTS 3,986,214  10/1976  Krasnor .................................... 3/13
4,159,546  7/1979  Shearing ................................... 3/13

FOREIGN PATENT DOCUMENTS 545352  5/1977  U.S.S.R. .................................... 3/13
563174  6/1977  U.S.S.R. .................................... 3/13
572267  9/1977  U.S.S.R. .................................... 3/13

*Primary Examiner*—Clifford D. Crowder
*Attorney, Agent, or Firm*—Fleit & Jacobson

[57] ABSTRACT

An artificial crystalline lens shaped as a lens provided with supporting and fastening elements. The fastening element is essentially a wire angle held at its ends to the lens lateral surface, while the supporting element is arranged on a diametrically opposite side of the lens. The vertex of the fastening wire angle lies on a line passing through the midpoint of the supporting element and the center of the lens. The supporting element is made of an elastic wire so as to make it possible to adjust the distance from the center of the lens to the supporting wire element. A novel method of implanting the artificial crystalline lens is also the subject of the present invention.

5 Claims, 6 Drawing Figures

ARTIFICIAL CRYSTALLINE LENS

The present invention relates to medicine and more specifically to ophthalmology, having particular reference to an artificial crystalline lens and a method of implanting same.

One of the most important problems in ophthalmological practice is one of correcting the vision after cataract extraction. There exist a number of methods of such correction, e.g., spectacles or contact lenses. However, in the case of correction with the aid of spectacles the patient fails to obtain an optimum vision, while correction with the help of contact lenses is far from being tolerated adequately well by any patient, especially by advanced-age ones, wherein the incidence of cataract is as high as 80 to 85 percent.

That is why the scientists of many countries were engaged in search for new ways of solving the above-discussed problem; one of such ways was an intraocular correction or implantation of an artificial crystalline lens.

Known in the present state of the art are various constructions of artificial crystalline lenses adapted to suit various operational procedures and techniques.

Thus, for instance, one prior-art artificial crystalline lens is known to comprise a lens provided with fastening and supporting elements, both of said elements being substantially similar and being essentially loop-shaped lugs of a stiff material held to the lens lateral surface, the only difference between said elements residing in that the fastening element has two projections adapted for guiding and retaining the suture material (cf. USSR Inventor's Certificate No. 563,174).

The crystalline lens of the character set forth hereinbefore is intended for being implanted in the crystalline capsule of the eye. However, when implanting such an artificial lens the centre and optical axis of the latter may prove to be offset with respect to the centre of the pupil and the optical axis of the eye due to the fact that crystalline capsule differs in size in various persons and may therefore frequently disagree with the linear dimensions of an artificial crystalline lens. It must be borne in mind that such a construction needs a pin-point production accuracy of structural components thereof, in particular, mutual arrangement of the lugs of the fastening element, as any displacement of these will result in mispositioning of the lens and, hence, in an inaccurate orientation thereof with respect to the vertical meridian of the eye.

The afore-discussed artificial crystalline lens is fitted in position as follows.

After having slit open the anterior chamber of the eye one must make an incision at the root of the iris, whereupon the anterior capsule of the crystalline lens is incised through an opening formed in the iris beforehand; next the nucleus of the lens and the lenticular masses are removed, after which an opening is made in the anterior chamber of the lens, and an artificial crystalline lens is implanted in the crystalline capsule, whereupon the lugs of the fastening element are stitched to the margins of the incision in the iris.

The aforesaid operation is disadvantageous in that the anterior capsule may be ruptured if the supporting element interferes with the edges of the capsule opening, and that no provision is made for an individual matching of an artificial crystalline lens to suit the size of the patient's crystalline capsule.

It is a general and essential object of the present invention to provide such fastening and supporting elements of an artificial crystalline lens as to make possible a reliable orientation thereof with respect to the vertical meridian of the eye.

It is another object of the present invention to reduce the production accuracy tolerance of the supporting element and make its mounting in position simpler and easier.

One more important object of the present invention is to provide a possibility of attaining a complete fitness of the overall size of an artificial crystalline lens and the size of the patient's crystalline capsule.

One of the other objects of the present invention is to render possible a visual control over orientation of the lens axis relative to the vertical meridian of the eye.

And still another object of the present invention is to provide an optimum procedure for implanting the artificial crystalline lens of the character set forth hereinbefore.

Said and other objects are accomplished due to the fact that in an artificial crystalline lens, comprising a lens, fastening and supporting elements held thereto on the diametrically opposite sides thereof, said elements being adapted for setting said lens in the crystalline capsule of the patient's eye, according to the present invention the fastening element is a wire angle held to the lens lateral surface in such a manner that the vertex thereof lies on a line passing through the centre of the lens circumference and the midpoint of the supporting wire element also held to the lens lateral surface, said wire element being spread along the lens periphery and made of an elastic material so as to be radially displaceable in order to adjust the distance from the lens centre to the supporting wire element to suit the size of the crystalline capsule of the patient's eye.

An advantageous feature of the afore-discussed construction consists in that the mutual arrangement of the vertex of the fastening element, viz., wire angle, the supporting element and the centre of the lens at all times provides for a correct orientation relative to the vertical meridian of the eye, this being due to the fact that any cocking inherent in the prior-art construction is ruled out. In addition, radial displaceability of the supporting element on the one hand makes it possible to reduce production accuracy tolerance of said element and simplify its mounting in position, and on the other hand provides for a possibility of attaining a complete fitness of the overall size of an artificial crystalline lens and the size of the patient's crystalline capsule.

It is expedient that the wire angle be curved, nearby its vertex, in a direction perpendicular with the legs or sides thereof so that the vertex of the wire angle lies in a plane passing through the apex of the lens spherical surface, which enables one to avoid cocking of the lens in its vertical plane.

It is most expedient that the wire angle be curved so as to define an elbow bend one of whose arms being normal to the sides of the wire angle, while the other arm thereof is normal to the former arm of the elbow bend and lies in a plane passing through the apex of the lens.

An eyelet may be provided at the vertex of the wire angle for the suture material to pass through.

With a view to appropriately positioning the lens with respect to the vertical meridian of the eye, marks must be made on the lens, said marks lying on an imaginary line passing through the vertex of the wire angle and the midpoint of the supporting element and being spaced one-third the lens radius apart from the edge of the lens.

A method of implanting an artificial crystalline lens incorporates a basal iridotomy to form an opening in the iris, a preequatorial incision of the anterior crystalline capsule through said opening in the iris, removal of the contents of the crystalline capsule followed by cleaning the posterior capsule, measurement of the distance from the equator of the crystalline capsule to the centre of the pupil followed by a corresponding radial displacement of the supporting element of the artificial crystalline lens until the distance from the centre of the lens thereof gets substantially equal to said measured distance, bringing the artificial lens with its supporting element into the crystalline capsule making way through the opening resulting from said basal iridotomy and through said preequatorial incision in the anterior crystalline capsule, stitching the fastening element to the margins of the central portion of the basal iridotomy, making an incision in the central zone of the anterior capsule opposite to the pupil, whereupon the axis of the artificial crystalline lens is oriented against the vertical meridian of the patient's eye using the marks provided on the lens.

Such a method of implanting an artificial lens prevents the crystalline capsule from rupture and provides for matching of optimum overall size of said lens immediately during the operation.

Given below is a detailed disclosure of the present invention by way of exemplary embodiments of a constructional arrangement of the proposed artificial crystalline lens and an implanting procedure thereof to be considered in conjunction with the accompanying drawings, wherein.

Figures 1, 2:
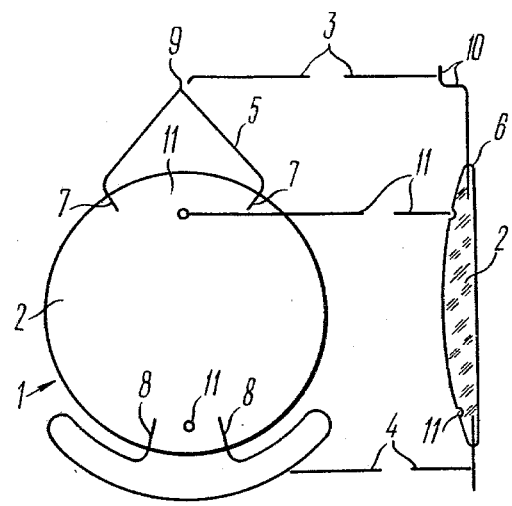
FIG. 1 is a front view of an artificial crystalline lens, according to the invention.
FIG. 2 is a side view of an artificial crystalline lens.

Now referring to FIG. 1 an artificial crystalline lens indicated as a whole at Ref. No. 1 comprises a lens 2 of any known construction, such as a planoconvex one as shown in FIG. 2, a fastening element 3 and a supporting element 4. The fastening element 3 is essentially an angle made of a wire 5 and built-in with its ends 7 into a peripheral lateral surface 6 of the lens 2 by any known method. Situated on a diametrically opposite side of the lens is the supporting element 4 which is in effect a loop-shaped lug made of an elastic wire, say, one of a platinum-iridium alloy, said element being built-in with its ends 8 into the lateral lens surface similarly to the ends 7 of the fastening element.

The fastening element made as the wire angle 3 and the lug-shaped supporting element 4 are so arranged that a vertex 9 of the wire angle lies on a line passing through the centre of the lens 2 and the midpoint of the supporting element 4.

The top portion of the wire angle is curved transversely towards the apex of the lens 2, with the result that an elbow bend 10 is formed, as can be seen distinctly from FIG. 2, said elbow bend having two arms of which one is normal to the sides of the wire angle, while the other arm is normal to the former arm and lies in a plane passing through the apex of the lens spherical surface.

In addition one can see from FIGS. 1 and 2 point-marks 11 are made on the lens spaced one-third its radius from the edge thereof and lying on a line passing through the vertex of the wire angle 3 and the midpoint of the lug 4.

Figure 3:
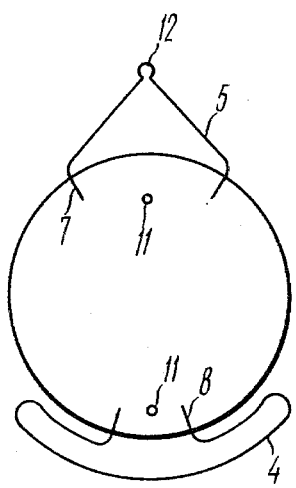
FIG. 3 is a view of another embodiment of an artificial crystalline lens.

FIG. 3 illustrates an artificial crystalline lens substantially similar to that shown in FIGS. 1 and 2 and therefore having the same reference numerals, the sole difference between said lenses residing in that an eyelet 12 is provided at the vertex of the wire angle for the suture material to pass through.

Now let us consider the operational procedure involved in fitting such an artificial crystalline lens in position.

Figure 4:
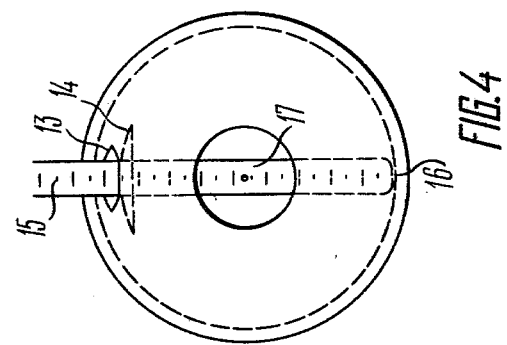
FIG. 4 shows symbolically the patient's eye while measuring the parameter of the crystalline capsule.

The implanting of an artificial crystalline lens in the crystalline capsule of a patient is carried out as follows. Once an extracapsular extraction of the cataract has been performed a special calibrated spatula 15 is brought into the empty crystalline capsule through a basal iridotomy 13 (FIG. 4) and a preequatorial incision 14 of the anterior capsule. Then the end of the spatula 15 is let go as far as an equator 16 in the eye bottom portion (at six o'clock), and the distance to the centre 17 of the pupil.

Figure 5:
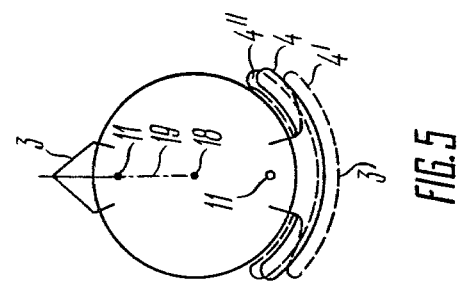
FIG. 5 is a view of an artificial crystalline lens while being prepared for implanting.

The supporting element of the artificial crystalline lens, made as the loop-shaped lug 4 (FIG. 5) is either bent out or bent in so as to obtain a distance to a centre 18 of the lens, corresponding to the distance from the equator of the crystalline capsule to the centre of the pupil.

Figure 6:
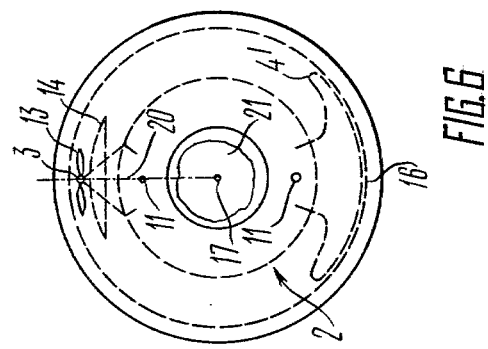
FIG. 6 illustrates a mutual arrangement of an artificial crystalline lens in the crystalline capsule of the patient's eye and the centre of the pupil after the lens having been oriented against the vertical meridian of the eye.

After matching the lens of a required size it is introduced into the crystalline capsule through the basal iridotomy 13 (FIG. 6) and the preequatorial incision 14 in the anterior capsule so that the loop-shaped lug 4 should reach the equator 16 of the crystalline capsule in the bottom eye portion, and the wire angle 3 with an elbow bend is stitched up to the margins of the basal iridotomy. Then an opening is made in an anterior capsule 20 of the crystalline capsule within the zone of the pupil, using a diamond blade or Vannas's scissors.

An axis 19 of the artificial crystalline lens is oriented to the vertical meridian of the eye along the line passing through the vertex of the wire angle and the point-marks 11 on the lens 2 depending upon whether said axis deviates from the normal (vertical) position, whereby the centre 18 of the lens is brought in alignment with the centre 17 of the pupil.

The implantation terminates in hermetically sealing the operative incision and restoration of the anterior chamber with a balanced solution. Then the eyeball is irrigated with an atropine solution, whereas some antibiotics and corticosteroids are medicated under the bulbar conjunctiva.

For the sake of example given below are two case histories.

Patient A., male, aged 22. a car driver. Admitted to the eye clinic on June 27, 1978 with a diagnosis of a traumatic cataract of the right eye. The affected eye shows a scar of the cornea; the left eye is sound and emmetropic.

Status on admission was as follows.

Right eye: acuity of vision at the level of photoreception with a correct projection, autoophthalmoscopy and cobalt test are positive, $P_o=13$ mm Hg.

The adnexa oculi remain unchanged, the conjunctiva is quiet. The cornea shows a small scar passing throughout all layers. The anterior chamber is not as deep as that of the left eye. The iris exhibits no changes. The pupil is round, of a medium width, reacts to light vividly. The crystalline lens is opalescent throughout all layers and shows the symptoms of intumescence. The angle of the anterior chamber is open, of a medium width, the trabecula is not pigmented. Electronic tonography evidence: $P_o=13$; $C=0.34$; $F=0.595$; $P_o/C=38.2$. Findings of echobiometry; the length of the antero-posterios axis of the eye is 23.32 mm; the refraction of the cornea is 44 diopters. An artificial crystalline lens was made, having an optical refractive power of 61.9 dioptres (as measured in the air).

Left eye: no pathological changes. The acuity of vision equals 1.0.

The operation of the right eye performed on June 28, 1978 was one of an intracapsular implantation of an artificial crystalline lens by the afore-described procedure. During the operation a 1-percent atropine solution was several times introduced into the eye operated upon.

The clinical coursing of the postoperative period was as follows.

In the day of operation the patient was permitted to walk and take food normally; the following treatment was instituted: eye drops three times a day, viz., a one-percent atropine solution, corticosteroids and some disinfectants; Butadion and Dimedrol were administered perorally in a dose of one tablet of each drug three times a day.

The state of the eye operated upon:

in the day of the operation—hyperemia of the conjunctiva, the corneal incision is well adapted with a continuous supramid suture (ten noughts); an inconsiderable descemetitis is observed; the anterior chamber is deep, the aqueous humour is transparent. The iris is quiet, the pupil is 3 mm wide, round in shape; iridotomy is seen at the upper edge of the limbus corneae at 12 o'clock, the supporting element of the implanted artificial crystalline lens being stitched up to the margin of the incised iris at the midpoint thereof; the artificial crystalline lens is seen to assume a normal position in the crystalline capsule, the position of its axis with respect to the vertical meridian of the eye is right.

Within the following days after the operation (from the 1st to the 5th) the hyperemia of the conjunction nearly disappeared, the pupil dilated to 6.5 mm in diameter, round in shape; there is seen against the reflex of the fundus oculi the entire artificial lens and the ends of the supporting and fastening elements built-in into its edge; there are also seen the point-marks on the lens a dia. 3.5 mm opening in the anterior capsule, showing irregular margins. The posterior capsule is spaced somewhat apart from the posterior lens surface. The vitreous body is transparent. The fundus oculi shows the optic disk, the yellow spot and the periphery without any pathological changes.

Status on dismissal on July 3, 1978 was as follows. The acuity of vision equals 0.4 with correction ($-$cyl $2.0^D$), 0.8.

On Sept. 13, 1978 the corneal suture was removed. The accuity of vision equals 0.9 with correction ($+0.5^D$), 1.0.

The right eye is quiet, the scar on the cornea is scarcely seen. The anterior chamber is deep, the aqueous humor is transparent. The pupil is round at the centre, 2.5 mm in diameter, reacts to light normally. The margins of the opening in the anterior capsule are not seen. An incision in the iris is seen at 12 o'clock in the limbus cornease, with the fastening element stitched up to the margins thereof. No iridodonesis is observed.

The artificial lens is seen within the zone of the pupil, the anterior and posterior surfaces of the lens are clean. The posterior capsule and the vitreous body are transparent. The optic disk, the yellow spot and the periphery of the fundus oculi show no changes.

Gonioscopy findings: the anterior chamber angle is wide, the trabecula is not pigmented, no adhesions at the corner are observed.

Electronic tonography findings: $P_o=15$; $C=0.4$; $F=1.5$; $P_o/C=37.5$.

The field of vision is normal. A binocular vision takes place.

The patient keeps working as a car driver and leads an ordinary mode of living without any restrictions as to physical work, or the attitude of the head and trunk. The observation period lasts 9 months.

Patient P., male, aged 78, a writer. Admitted to the eye clinic on Dec. 15, 1976 with a diagnosis of an immature scyphoid cataract on the right eye and a primary cataract on the left eye.

Status on admission:

The acuity of vision: of the right eye, at the level of photoreception with a correct projection; of the left eye, 0.6, the visual acuity fails to be improved by correction.

Right eye—the adnexa oculi remain unchanged, the conjunctiva is quiet; the cornea is lustrous and transparent; the anterior chamber is of a medium depth, the aqueous humor is transparent; the iris is subatrophic; the pupil is round, 2 mm in diameter; opalescence in the lens is mostly localized under the posterior capsule. The fundus oculi is not amenable to ophthalmoscopic examination. $P_o=14$; $C=0.15$; $F=0.41$; $P_o/C=93$. Autoophthalmoscopy and cobalt test are positive. Gonioscopic examination shows the angle of the anterior chamber to be of a medium width. The trabecula is moderately pigmented. The refraction of the cornea is 44.5 dioptres. Echobiometry shows the length of the anteroposterior axis of the eye to be 24.1 mm. An artificial crystalline lens with an optical refractive power of 61 dioptres (in the air) was custom-made. The left eye exhibits but inconsiderable changes in the lens under the posterior capsule.

The operation of the right eye carried out on Dec. 16, 1976 was one of an intracapsular implantation of an artificial crystalline lens by the aforedescribed procedure.

Both the operation and the postoperative period were uneventful.

The clinical coursing of the postoperative period was as follows.

In the day of operation the patient was allowed to walk and take food normally. The treatment instituted: eye drops three times a day, corticosteroids, disinfectant and vitamin drops. Administered perorally were Butadion (0.15 g). and Dimedrol (0.05 g) in tablet form in a dose of one tablet of each drug three times a day.

Forasmuch as a hypertensive syndrome was observed in the patient in the first day after the operation, he was administered Diacarb in a dose of 0.25 g twice a day for two days, whereupon the intraocular pressure returned to normal and has remained normal since then.

The state of the eye operated upon;

in the day of the operation—the conjunctiva is hyperemic, the corneal epithelium is edematous, descemetities is observed. The edema of the corneal epithelium disappeared on the 3rd day, descemetitis on the 4th day (the day of dismissal) after the operation. The corneal incision is adapted well by a continuous supramid suture (ten noughts). The anterior chamber is deep; a gradually attenuated tyndallization was noted in said chamber for four days. The pupil is 3.5 mm wide, the incision of the iris is seen at the upper edge of the limbus corneae at 12 o'clock, showing the fastening element stitched up thereto. The implanted artificial lens is seen in the optical section within the zone of the pupil, its surfaces being clean.

Within the following days after the operation (from the 1st till the 4st) the hyperemia of the conjunctiva nearly disappeared, as well as the edema of the corneal epithelium, while the symptoms of descemetitis almost subsided. The pupil is round at the centre, 3.5 mm in diameter; no iridodonesis is observed; the margins of the opening in the anterior capsule are shown at the very edge of the pupil in some individual spots. The posterior capsule is transparent, as well as the vitreous body. The optic disk, the yellow spot and the periphery of the fundus oculi exhibit no changes.

Status on dismissal on Dec. 20, 1976: the visual acuity of the right eye equals 0.4 with correction $-cyl\ 5.0^D$ ax 180°.

Results of a repeated examination on Feb. 14, 1977:

The visual acuity of the right eye equals 0.2 with correction $-3.0^D = 0.9$; on Aug. 1, 1977 the visual acuity of the right eye was found to be 0.5 with correction $-0.75^D \bigcirc cyl -2.0^D$ ax $95° = 1.25$.

Upon an examination carried on Aug. 1, 1977 the following data were obtained.

Right eye is quiet, the scar in the corneal portion of the limbus cornea is barely seen. The cornea is lustrous and transparent. The anterior chamber is deep, the aqueous humor is transparent. The iris is subatrophic. The pupil is round at the centre, 2 mm in diameter. An incision of the iris is seen in the limbus corneae at 12 o'clock (only with the upper lid raised), showing the fastening element stitched up thereto. The implanted artificial lens is seen in the zone of the pupil, its surfaces being clean. The posterior capsule is transparent and is spaced somewhat apart from the posterior lens surface. The vitreous body is transparent. The fundus oculi exhibits the optic disk, the yellow spot and the periphery without any pathological changes.

Gonioscopy findings: the angle of the anterior chamber is wide, the trabecula is moderately pigmented, no adhesions at the corner are observed.

Electronic tonography findings: $P_o = 16$; $C = 0.3$; $F = 1.42$; $P_o/C = 53$.

The field of vision is normal.

Left eye: the visual acuity decreased to 0.2 and fails to be corrected due to an intensified opalescence of the lens.

The patient continues to work as a writer, goes skiing, visits regularly the swimming pool. The observation period 2 years and 3 months.

What we claim is:

1. In an artificial crystalline lens adapted for being implanted in a patient's eye and comprising a lens and fastening and supporting elements held to the lens on diametrically opposite edge portions of the lens lateral surface, said elements being adapted for setting said lens in the crystalline capsule of the patient's eye, the improvement comprising the fastening element being a wire angle held to the lens lateral surface in such a manner that its vertex lies on a line passing through the lens circumference, and said supporting element being held to the lateral lens surface and being spread along the lens periphery and made of an elastic wire so as to be radially displaceable in order to adjust the distance from the lens centre to the supporting wire element to suit the size of the crystalline capsule of the patient's eye, the supporting element having a midpoint lying on a common line with the vertex of the wire angle, the common line passing through the midpoint of the lens, the wire angle being curved, near its vertex, in a direction perpendicular to the sides thereof so that the vertex of the wire angle lies in a plane containing the apex of the lens sperical surface.

2. An artificial crystalline lens as claimed in claim 1, wherein an eyelet is provided at the vertex of the wire angle for passage of suture material.

3. An artificial crystalline lens as claimed in claim 1, wherein marks are made on the lens, said marks lying on an imaginary line passing through the vertex of the wire angle and the midpoint of the supporting element and being spaced one-third the lens radius from the lens edge.

4. In an artificial crystalline lens adapted for being implanted in a patient's eye and comprising a lens and fastening and supporting elements held to the lens on diametrically opposite edge portions of the lens lateral surface, said elements being adapted for setting said lens in the crystalline capsule of the patient's eye, the improvement comprising the fastening element being a wire angle held to the lens lateral surface in such a manner that its vertex lies on a line passing through the lens circumference, and said supporting element being held to the lateral lens surface and being spread along the lens periphery and made of an elastic wire so as to be radially displaceable in order to adjust the distance from the lens centre to the supporting wire element to suit the size of the crystalline capsule of the patient's eye, the supporting element having a midpoint lying on a common line with the vertex of the wire angle, the common line passing through the midpoint of the lens, the wire angle being curved, near its vertex, so as to define an elbow bend having a first arm normal to legs of the wire angle, and a second arm thereof normal to the first arm of the elbow bend and lying in a plane containing the apex of the lens.

5. A method of implanting an artificial crystalline lens having fastening and supporting elements held on diametrically opposite edge portions of the lens lateral surface, the method incorporating a basal iridotomy to form an opening in the iris, a preequatorial incision of the anterior crystalline capsule through said opening in the iris, removal of the contents of the crystalline capsule followed by cleaning the posterior capsule, said method comprising measuring the distance from the equator of the crystalline capsule to the centre of the pupil, radially displacing the supporting element of the artificial crystalline lens until the distance from the centre of the lens thereof substantially equals said measured distance, inserting the artificial lens with its supporting element into the crystalline capsule through the opening resulting from said basal iridotomy and through said preequatorial incision in the anterior crystalline capsule, stitching the fastening element to the margins of the central portion of the basal iridotomy, making an incision in the central zone of the anterior capsule opposite to the pupil, and orienting the axis of the artificial crystalline lens against the vertical meridian of the patient's eye, the lens having marks provided thereon for the orienting thereof.

* * * * *